(12) United States Patent
Kassab

(10) Patent No.: US 10,456,060 B2
(45) Date of Patent: Oct. 29, 2019

(54) DEVICES FOR DETECTING ORGAN CONTENTS USING IMPEDANCE AND METHODS OF USING THE SAME TO PROVIDE VARIOUS THERAPIES

(71) Applicant: Ghassan S. Kassab, Zionsville, IN (US)

(72) Inventor: Ghassan S. Kassab, Zionsville, IN (US)

(*) Notice: Subject to any disclaimer, the term of this patent is extended or adjusted under 35 U.S.C. 154(b) by 118 days.

(21) Appl. No.: 13/775,099

(22) Filed: Feb. 22, 2013

(65) Prior Publication Data

US 2013/0267867 A1    Oct. 10, 2013

Related U.S. Application Data

(60) Provisional application No. 61/601,608, filed on Feb. 22, 2012.

(51) Int. Cl.
*A61B 5/053* (2006.01)
*A61B 5/00* (2006.01)

(52) U.S. Cl.
CPC ............ *A61B 5/053* (2013.01); *A61B 5/4238* (2013.01); *A61B 5/0002* (2013.01); *A61B 5/4836* (2013.01)

(58) Field of Classification Search
CPC ..... A61B 5/053; A61B 5/4836; A61B 5/4238; A61B 5/0002
USPC ....................................................... 600/547
See application file for complete search history.

(56) References Cited

U.S. PATENT DOCUMENTS

| | | | | |
|---|---|---|---|---|
| 5,105,826 A | * | 4/1992 | Smits | A61N 1/0587 600/374 |
| 5,109,870 A | * | 5/1992 | Silny et al. | 600/593 |
| 5,353,802 A | * | 10/1994 | Ollmar | 600/547 |
| 5,544,662 A | * | 8/1996 | Saulnier et al. | 600/547 |
| 8,078,274 B2 | | 12/2011 | Kassab | |
| 2001/0051774 A1 | * | 12/2001 | Littrup et al. | 600/547 |
| 2005/0203433 A1 | * | 9/2005 | Singer | 600/547 |
| 2006/0136028 A1 | * | 6/2006 | Ross | A61N 1/0587 607/129 |
| 2006/0161073 A1 | * | 7/2006 | Singer et al. | 600/547 |
| 2008/0039718 A1 | * | 2/2008 | Drinan et al. | 600/427 |
| 2008/0200802 A1 | * | 8/2008 | Bhavaraju et al. | 600/426 |
| 2008/0287788 A1 | * | 11/2008 | Richardson et al. | 600/437 |
| 2008/0294041 A1 | * | 11/2008 | Kassab | A61B 5/02007 600/433 |
| 2009/0026077 A1 | * | 1/2009 | Dopp | G01N 27/28 204/415 |
| 2009/0182287 A1 | | 7/2009 | Kassab | |
| 2010/0030055 A1 | * | 2/2010 | Kassab | 600/374 |
| 2010/0160745 A1 | * | 6/2010 | Hills et al. | 600/301 |
| 2010/0305468 A1 | * | 12/2010 | Policker | A61N 1/36007 600/547 |
| 2010/0324432 A1 | * | 12/2010 | Bjorling | A61N 1/36007 600/504 |

* cited by examiner

*Primary Examiner* — Patrick Fernandes
(74) *Attorney, Agent, or Firm* — Reichel Stohry Dean LLP; Mark C. Reichel; Natalie J. Dean

(57) ABSTRACT

Devices for detecting organ contents using impedance and methods of using the same to provide various therapies. In an exemplary embodiment of a device for detecting organ contents of the present disclosure, the device comprises a body having a detector coupled thereto, the device configured for placement at or near an outside of an organ and operable to detect contents on an inside of the organ using impedance.

20 Claims, 4 Drawing Sheets

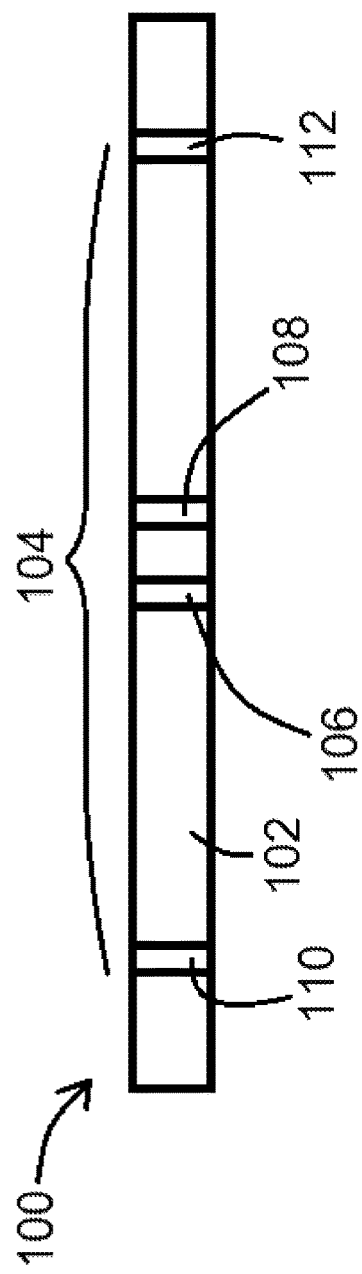
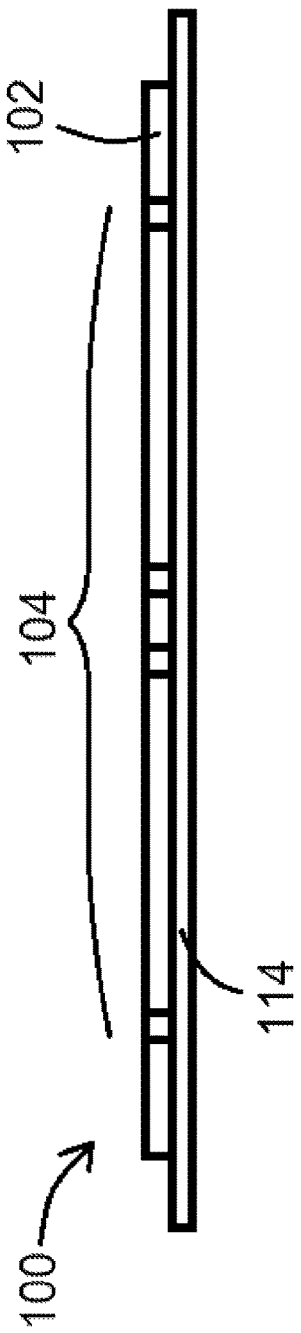

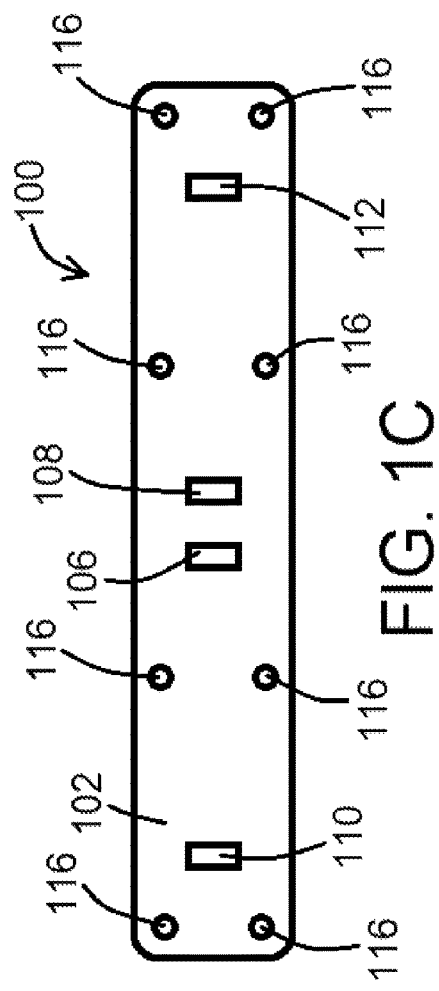
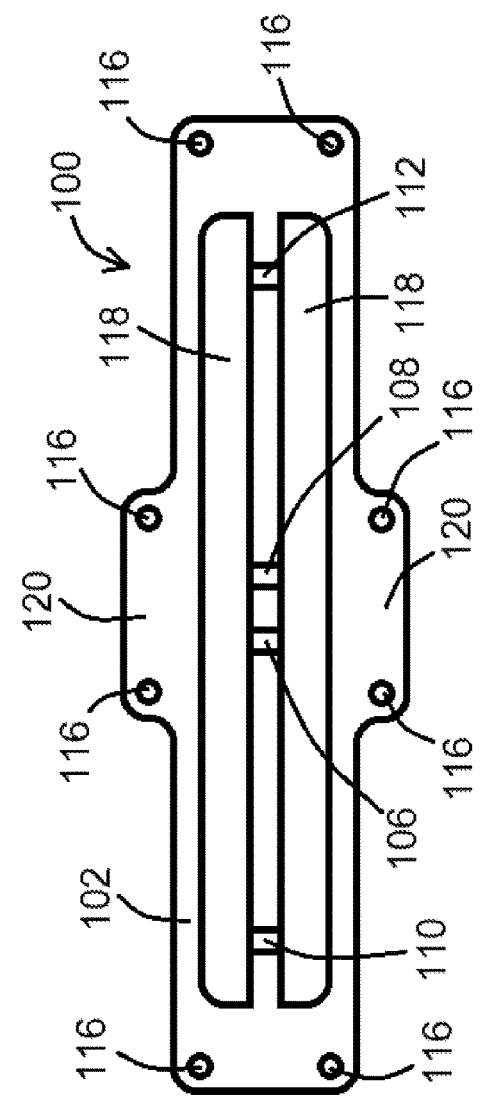

DEVICES FOR DETECTING ORGAN CONTENTS USING IMPEDANCE AND METHODS OF USING THE SAME TO PROVIDE VARIOUS THERAPIES

PRIORITY

The present application is related to, and claims the priority benefit of, U.S. Provisional Patent Application Ser. No. 61/601,608 filed Feb. 22, 2012, the contents of which are hereby incorporated by reference in their entirety into this disclosure.

BACKGROUND

Current technologies used to detect ingestion of food and drink within a stomach involve the placement of some sort of device or sensor within the stomach itself to detect temperature. If a person using such a device drinks a cold beverage, for example, the device would detect a decrease in temperature, which would then increase in a matter of seconds due to the warming of the beverage within the person's stomach. While such devices may work to detect initial temperature changes, such devices are placed by puncturing the stomach, which is traumatic and can lead to surgical and other complications. Furthermore, and over time, stomach acids can corrode the device or sensor itself, causing it to fail over time and potentially releasing harmful chemical byproducts due to the reaction of metallic componentry, for example.

As such, it would be beneficial to have a non-invasive device, system, and method for detecting contents of an organ and to be able to use the same to detect certain types of contents from one another that does not have the aforementioned shortcomings.

BRIEF SUMMARY

In an exemplary embodiment of a device for detecting organ contents of the present disclosure, the device comprises a body having a detector coupled thereto, the device configured for placement at or near an outside of an organ and operable to detect contents on an inside of the organ using impedance. In another embodiment, the body is elongated. In yet another embodiment, the body is configured as a patch. In an additional embodiment, the detector comprises at least four electrodes. In yet an additional embodiment, the detector comprises a pair of detection electrodes positioned in between a pair of excitation electrodes.

In an exemplary embodiment of a device for detecting organ contents of the present disclosure, the pair of excitation electrodes are spaced apart from one another sufficient to generate a field that extends to the inside of the organ. In an additional embodiment, the pair of detection electrodes is capable of detecting the field generated by the pair of excitation electrodes. In yet an additional embodiment, the detector is operable to detect whether or not the inside of the organ has a liquid content therein. In another embodiment, the detector is operable to detect changes in an amount of the liquid content inside of the organ.

In an exemplary embodiment of a device for detecting organ contents of the present disclosure, the detector is operable to detect whether or not the inside of the organ has a solid content therein. In another embodiment, the detector is operable to detect changes in an amount of the solid content inside of the organ. In yet another embodiment, the device further comprises an adhesive pad coupled to the body, the adhesive pad configured to secure the device to the outside of the organ. In an additional embodiment, the device further comprises at least one suture aperture defined within the body, the at least one suture aperture sized and shaped to receive at least one suture therethrough to secure the device to the outside of the organ. In yet an additional embodiment, the body has at least one rounded portion.

In an exemplary embodiment of a device for detecting organ contents of the present disclosure, the device further comprises at least one detector aperture defined within the body, the at least one detector aperture sized and shaped to minimize interference that would compromise data obtained by the detector. In an additional embodiment, the device further comprises at least one tab extending from the body. In yet an additional embodiment, the device further comprises at least one suture aperture defined within the at least one tab, the at least one suture aperture sized and shaped to receive at least one suture therethrough to secure the device to the outside of the organ. In another embodiment, the device further comprises a first suture aperture defined within the at least one tab, and a second suture aperture defined within the body, the at least one suture aperture sized and shaped to receive at least one suture therethrough to secure the device to the outside of the organ.

In an exemplary embodiment of a device for detecting organ contents of the present disclosure, the device further comprises a power source operably connected to the detector, the power source configured to provide power to the detector so to operate the detector. In another embodiment, the power source is coupled to the body of the device. In yet another embodiment, the power source is positioned within a patient's body when the device is positioned at or near the outside of the organ of the patient within the patient's body. In an additional embodiment, the power source is positioned outside of a patient's body when the device is positioned at or near the outside of the organ of the patient within the patient's body.

In an exemplary embodiment of a device for detecting organ contents of the present disclosure, the device further comprises an internal memory operably connected to the detector, the internal memory operable to store conductance data obtained by the detector. In an additional embodiment, the device further comprises a transmitter operably connected to the detector, the transmitter operable to transmit conductance data from the detector to an external system. In yet an additional embodiment, when the device is device is positioned at or near the outside of the organ of the patient within the patient's body, the device is operable to transmit conductance data obtained by the detector to a data acquisition and processing system.

In an exemplary embodiment of a device for detecting organ contents of the present disclosure, the data acquisition and processing system is directly coupled to the device. In another embodiment, the data acquisition and processing system is positioned within the patient's body when the device is positioned within the patient's body. In yet another embodiment, the data acquisition and processing system is positioned outside of the patient's body when the device is positioned within the patient's body. In an additional embodiment, the data acquisition and processing system is in wireless communication with the device.

In an exemplary embodiment of a method for using a device of the present disclosure, the method comprises the steps of positioning a device at or near an outside of an organ of a patient within the patient's body, the device comprising a body having a detector coupled thereto, the device operable to detect contents on an inside of the organ using impedance, and operating the device to detect contents on the inside of the organ. In another embodiment, the positioning step is performed laparoscopically. In yet another embodiment, the operating step is performed by activating the detector to obtain conductance data, the conductance data indicative of the contents on the inside of the organ. In an additional embodiment, the operating step yields conductance data from the detector, the conductance data indicative of a liquid content on the inside of the organ. In yet an additional embodiment, the operating step yields conductance data from the detector, the conductance data indicative of a change in an amount of a liquid content on the inside of the organ.

In an exemplary embodiment of a method for using a device of the present disclosure, the operating step yields conductance data from the detector, the conductance data indicative of a solid content on the inside of the organ. In an additional embodiment, the operating step yields conductance data from the detector, the conductance data indicative of a change in an amount of a solid content on the inside of the organ. In yet an additional embodiment, the positioning step is performed to position the device at or near the outside of an organ selected from the group consisting of a stomach, an intestine, a bladder, a lung, and a heart. In another embodiment, the operating step yields conductance data from the detector, the conductance data indicative of a change in an amount of a liquid content on the inside of the organ.

In an exemplary embodiment of a method for using a device of the present disclosure, the method further comprises the step of administering a therapy to the patient based upon the contents detected on the inside of the organ. In another embodiment, the step of positioning a device is performed by positioning the device at or near the outside of the patient's stomach, and wherein the step of administering a therapy is performed to assist the patient with weight loss. In yet another embodiment, the step of positioning a device is performed by positioning the device at or near the outside of the patient's stomach, and wherein the step of administering a therapy is performed to assist the patient with appetite control. In an additional embodiment, the step of positioning a device is performed by positioning the device at or near the outside of the patient's lungs, and wherein the step of administering a therapy is performed to treat an instance of fluid retention within lungs of the patient.

In an exemplary embodiment of a method for using a device of the present disclosure, the step of positioning a device is performed by positioning the device at or near the outside of the patient's intestines, and wherein the step of administering a therapy is performed to assist the patient with digestion. In an additional embodiment, the step of positioning a device is performed by positioning the device at or near the outside of the patient's intestines, and wherein the step of administering a therapy is performed to assist the patient with excretion. In yet an additional embodiment, the step of positioning a device is performed by positioning the device at or near the outside of the patient's bladder, and wherein the step of administering a therapy is performed to assist the patient with urination. In another embodiment, the step of positioning a device is performed by positioning the device at or near the outside of the patient's bladder, and wherein the step of administering a therapy is performed to treat a urinary disorder of the patient. In yet another embodiment, the step of positioning a device is performed by positioning the device at or near the outside of the patient's heart, and wherein the step of administering a therapy is performed to treat a cardiac disorder of the patient.

In an exemplary embodiment of a system for detecting organ contents of the present disclosure, the system comprises an exemplary device of the present disclosure and an exemplary external system of the present disclosure.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 1A shows a top view of a device for detecting organ contents, according to an exemplary embodiment of the present disclosure;

FIG. 1B shows a side view of a device for detecting organ contents, according to an exemplary embodiment of the present disclosure;

FIG. 1C shows a top view of a device for detecting organ contents having suture apertures defined therein, according to an exemplary embodiment of the present disclosure;

FIG. 1D shows a top view of a device for detecting organ contents having two tabs and detector apertures defined therein, according to an exemplary embodiment of the present disclosure;

Figure 2:
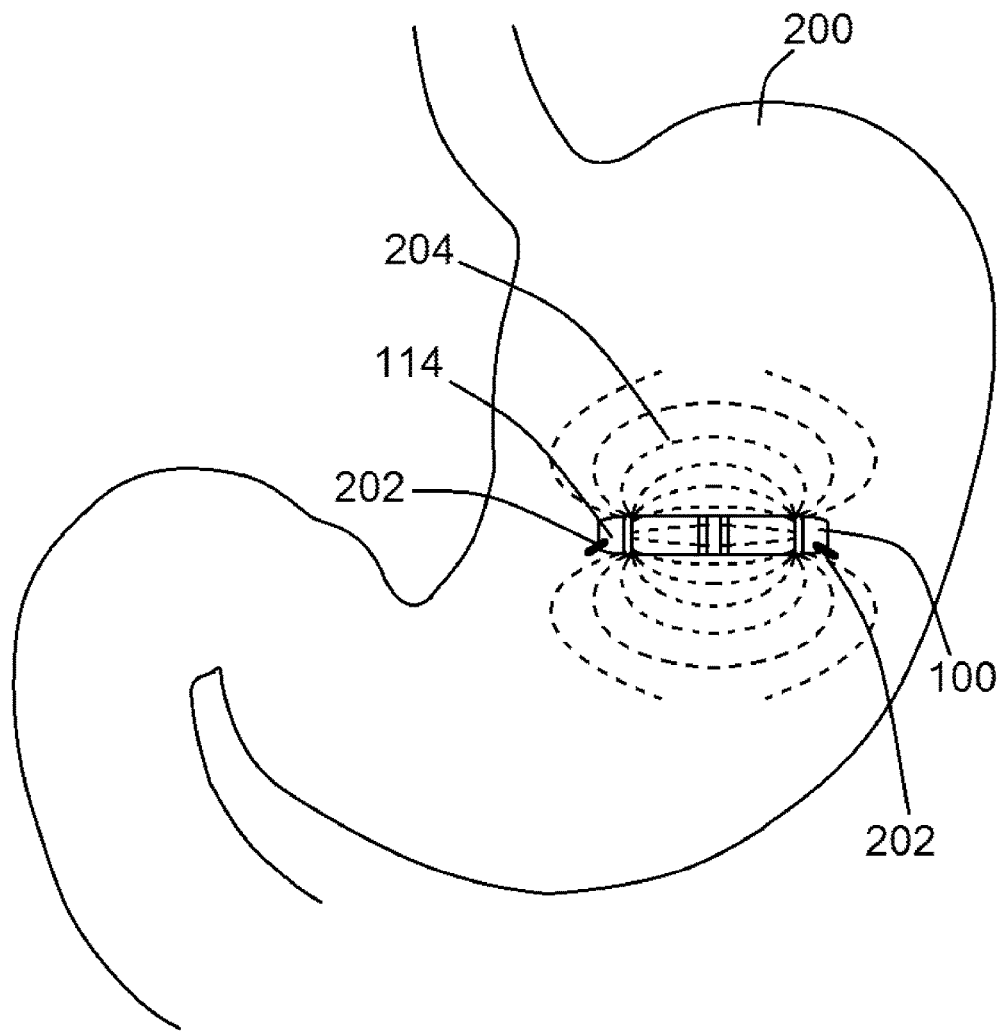
FIG. 2 shows a device for detecting organ contents positioned upon or relative to a stomach and operating to generate a field, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

An exemplary device for detecting organ contents of the present disclosure is shown in FIG. 1A. As shown in the top view of an exemplary device 100 shown in FIG. 1, device 100 comprises a body 102 having a detector 104 coupled thereto. Body 102, in various embodiments, can be elongated, have a patch configuration, or some other configuration suitable to allow detector 104 to be coupled thereto.

Detector 104, in at least one embodiment and as shown in FIG. 1A, can itself comprise a tetrapolar arrangement of electrodes with electrode spacings suitable to allow conductance measurements to be made through a wall of an organ 200, as shown in FIG. 2. For example, and as shown in FIG. 1A, an exemplary detector may comprise two detection electrodes 106, 108 positioned in between two excitation electrodes 110, 112, whereby detection electrodes 106, 108 can detect a field generated by excitation electrodes 110, 112.

Given the position of device 100 relative to an organ 200 (and on the outside of organ 200 as discussed in further detail herein) and the spacings of the electrodes 106, 108, 110, 112 of detector 104, detector 104 can identify differences in the content of organ 200 over time. For example, an exemplary device 100 of the present disclosure can detect the difference between an empty (or relatively empty) stomach (an exemplary organ 200) and a stomach that has contents therein. In at least one embodiment, device 100 can distinguish between stomach contents, such as whether or not a stomach has a liquid content or a solid content. In another embodiment, device 100 can detect changes in the amount of a liquid content or a solid content over time.

FIG. 1B shows a side view of another exemplary embodiment of a device 100 of the present disclosure. As shown in FIG. 1B, device 100 comprises a body 102 (which is shown as being elongated, but can be any number of other configurations) and a detector 104 coupled thereto. The embodiment shown in FIG. 1B also shows a material 114 coupled thereto, such as an adhesive pad, to facilitate placement of device 100 on the outside of a stomach (or other organ 200).

FIGS. 1C and 1D show other embodiments of devices 100 of the present disclosure. As shown in FIG. 1C, an exemplary device 100 of the present disclosure comprises a body 102 that is not as elongated as the embodiment shown in FIG. 1A, and having a general patch configuration. Detection electrodes 106, 108 are shown positioned within excitation electrodes 110, 112, and body 102 has a plurality of suture apertures 116 defined therein to allow one or more sutures 202, as shown in FIG. 2, to be used to secure device 100 to organ 200. Sutures 202 can be positioned directly through body 102 of device 100 (whereby the user positioning device 100 forces sutures 202 through body, such as with the use of a needle), and/or sutures 202 can be positioned through one or more suture apertures 116 defined within body 100 as shown in FIG. 2. So to minimize the potential of trauma to organ 200, body 102 can have a relatively straight and/or rounded configuration, as shown in FIG. 1C, so that no sharp corners exist that could cause damage to organ 200.

The exemplary embodiment of device 100 shown in FIG. 1D has some similar features to the embodiment shown in FIG. 1C and described above, but has a number of different features as well. As shown in FIG. 1D, device 100 comprises a body 102 also having a patch configuration, a plurality of suture apertures 116 defined therein, and a pair of detection electrodes 106, 108 positioned in between a pair of excitation electrodes 110, 112. However, and unlike the embodiment shown in FIG. 1C, the device 100 embodiment shown in FIG. 1D comprises a pair of detector apertures 118 on either side of the effective detector (electrodes 106, 108, 110, 112). Detector apertures 118, in at least one embodiment, are defined within body 102 so to potentially minimize interference caused by body 102 when device 100 is operated as desired. In addition to the foregoing, device 100 comprises tabs 120 having suture apertures 116 defined therein, whereby tabs 120 offer an interventionalist placing device 100 within a patient added flexibility with respect to suturing or otherwise affixing device 100 to an organ 200 of interest.

FIG. 2 shows an exemplary device 100 of the present disclosure positioned externally upon a stomach. Such a placement, which can be made so that device 100 touches the stomach directly, so that device 100 contacts a material 114 (such as an adhesive pad, as discussed in further detail herein) that touches the stomach, or so that device 100 is positioned relative to, but does not actually touch, the outside of a stomach, would be made depending on the device 100 embodiment so that device 100 can operate as intended. When properly placed/positioned, device 100 can be operated to create a field 204 (using excitation electrodes 106, 108) useful to detect organ 200 contents or changes in organ 200 contents over time (using detection electrodes 110, 112).

Such an exemplary device 100, as well as other embodiments of devices 100 of the present disclosure, may be configured so that they can be securely positioned external to an organ 200. For example, and as introduced above, an adhesive pad (an exemplary material 114 of the present disclosure) could be positioned between device 100 and organ 200 to secure device 100 to organ 200. In another embodiment, no adhesive pad may be used, but instead an adhesive (another exemplary material 114) could be placed on one or both of device 100 and/or organ 200 to secure device 100 to organ.

Figure 3A:
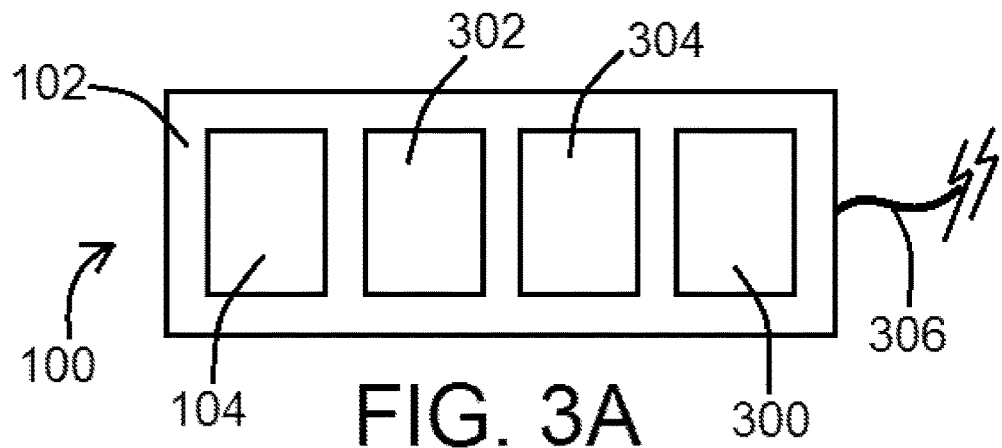
FIG. 3A shows a block diagram of components of a device for detecting organ contents, according to an exemplary embodiment of the present disclosure.
Figure 3B:
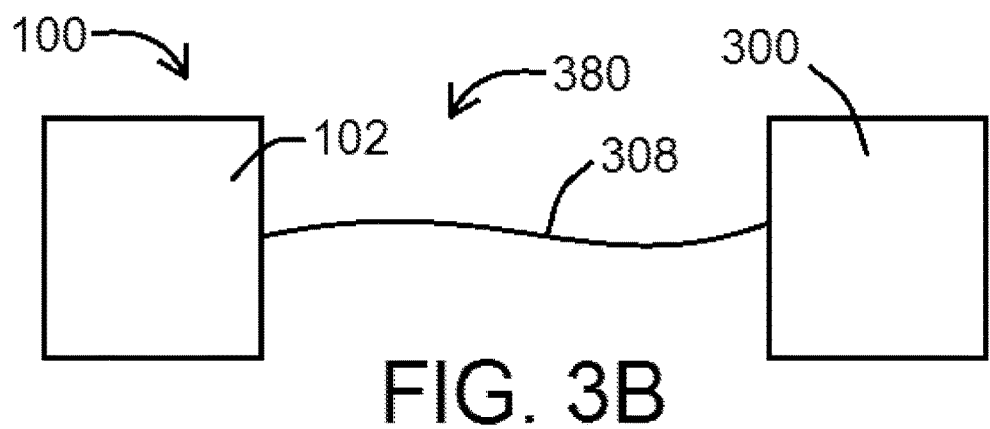
FIG. 3B shows a block diagram of a device for detecting organ contents coupled to a power source, according to an exemplary embodiment of the present disclosure.

FIGS. 3A and 3B show block diagrams of selected components of exemplary devices 100 of the present disclosure. For example, and as shown in FIG. 3A, an exemplary device 100 of the present disclosure includes a detector 104 and a power source 300, such as a battery, coupled directly to body 102 of device 100. Power sources 300, in various embodiments, are used to provide power to device 100 to operate certain electrodes 106, 108, 110, and/or 112, and potentially to transmit data to an internal memory 302 and/or to an external system in wired or wireless communication with device 100. In addition, and as shown in FIG. 3A, an exemplary device 100 of the present disclosure can comprise a transmitter 304 to transmit conductance data to an external system (such as an external data acquisition and processing system 350 shown in FIG. 3C), whereby transmitter 304 operates wirelessly or via wire 306 coupled to external system 350 or a component thereof. Several other wires and/or connectors (not shown) may be used with various device 100 embodiments to connect to electrodes 106, 108, 110, and/or 112, power source 300, memory 302, transmitter 304, and/or various other components of device 100.

In at least another embodiment, and as shown in FIG. 3B, device 100 comprises a detector 104 and has a wired connection via power wire 308 to a power source 300 not directly coupled to body 104 of device 100. In such an embodiment, power source 300 may be positioned external to the user's body. In various embodiments, power sources 300 may comprise single-use batteries, rechargeable batteries, and/or other power sources known and used in the medical arts.

Figure 3C:
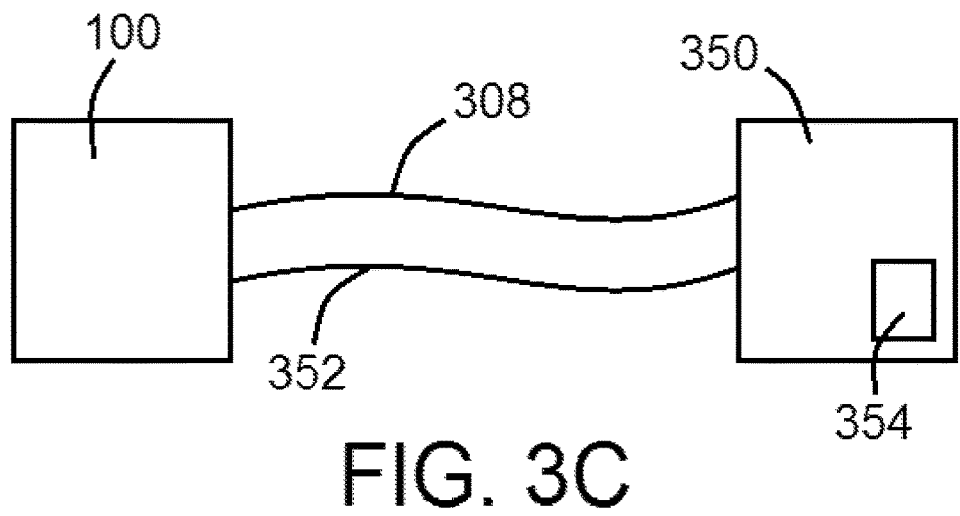
FIG. 3C shows a block diagram of a device for detecting organ contents coupled to a data acquisition and processing system, according to an exemplary embodiment of the present disclosure.

As shown in FIG. 3C and as initially referenced above, an exemplary device 100 of the present disclosure may be used with a wired (using a wire 352) or wireless connection to and from an external system 350, such as a data acquisition and processing system. In at least one embodiment, external system 350 comprises a processor 354 operable to operate electrodes 106, 108, 110, and/or 112 of device 100, receive conductance data therefrom, and process said data so that a user of device 100 is aware of device 100 operation in potential connection with one or more therapies to control or otherwise moderate or monitor ingestion of food and/or drink. As referenced herein, any number of device 100 embodiments may comprise any number of device components referenced herein so to generate an operable device 100.

In at least one exemplary embodiment of a system 380 of the present disclosure, and as shown in FIG. 3C, system 380 comprises an exemplary device 100 of the present disclosure and an exemplary external system 350 of the present disclosure. In various other embodiments, systems 380 may also include any number of other components of a device 100 of the present disclosure, as well as a power wire 308, a wire 352, and/or any number of other connectors.

Use of an exemplary device 100 of the present disclosure to detect stomach contents and/or changes thereto have a number of advantages as compared to other devices used or attempted to be used in the medical arts. First, and by either affixing an exemplary device 100 to a stomach or placing it in proximity to the stomach, device 100 can be operated to sense eating (the presence of fluid and/or solid food in the stomach) using impedance, without needing to penetrate the stomach wall or be positioned within the stomach. If the spacings of excitation electrodes 110, 112 sufficient so to generate a large field and to allow sensing of a large volume conductance by detection electrodes 106, 108, conductance measurements can allow monitoring of the stomach inputs.

Advantages to this approach include less overall trauma to the patient, as there is no need to penetrate the gastric wall. As device 100 is not positioned inside the stomach or within the stomach wall, there is no risk of device 100 corrosion (of the electrodes in particular), noting that other devices, such as those using thermistors within the stomach and relying on temperature changes to detect stomach content changes, are at risk of corrosion due to the acidic/corrosive nature of the stomach. In addition, conductance changes are much larger in amplitude than temperature differences, as an empty or relatively empty stomach with air will have nearly no conductivity. As such, it is easier to detect and analyze ingestion of food and/or drink as a trigger for initiation and ending of various therapies and ingestion pacing. Further, using conductance will allow for the differentiation between solid food, fluid, and air as they all have different electrical conductivity. Temperature measurements, on the other hand, do not discriminate between solid food, fluid, and air.

In addition, and by using conductance, the duration of the signal will last significantly longer given that food or liquid that changes the conductance will stay in the stomach longer, whereas temperature will equilibrate to body temperature relatively quickly (within seconds). This added flexibility with respect to detection allows for a greater degree of therapy to be made in proportion to the sustained degree of conductance change (i.e., the amount of food ingested) which cannot be done with temperature because it dissipates quickly (while conductance measurements are cumulative). Furthermore, the degree of therapy pacing can also be made to coincide with the sustained elevation of conductance. In various embodiments, it would be seamless to the sensing with the therapy delivery (given that this and pacing are both electrical), similar to an implantable cardioverter-defibrillator (ICD), which involves sensing of heart rate/rhythm with pacing therapy.

In at least one embodiment of a method for using a device 100 of the present disclosure, the method comprises the steps of positioning device 100 at or near an outside of an organ 200 of a patient within the patient's body, device 100 comprising a body 102 having a detector 104 coupled thereto, wherein device 100 is operable to detect contents on an inside of organ 200 using impedance, and operating device 100 to detect contents on the inside of organ 200. Device 100 may be positioned laparoscopically or via any number of surgical procedures. Detector 104, as referenced herein, can be activated to obtain conductance data, which is indicative of the contents on the inside of the organ. Such data can be indicative of a liquid content on the inside of organ 200, indicative of a change in an amount of a liquid content on the inside of organ 200, indicative of a solid content on the inside of organ 200, or indicative of a change in an amount of a solid content on the inside of organ 200, for example.

Device 100 can be positioned at or near the outside of any number of luminal organs, such as the stomach, intestine, bladder, lung, heart, blood vessels, and the like. Depending on the organ 200 being monitored, various types of therapies can be administered to the patient based upon the contents detected on the inside of organ 20. For example, if device 100 is positioned at or near the outside of the patient's stomach, the therapy that may be performed may be done so to assist the patient with weight loss and/or appetite control. If device 200 is positioned at or near the outside of the patient's lungs, the therapy that may be performed may be done so to treat the patient with an instance of fluid retention within his or her lungs.

Device 100 may be used with other organs 200 as well. For example, device 200 can be used to monitor intestine contents, with data useful to treat or assist a patient with digestion and/or excretion. For example, and regarding potential instances of rectal incontinence, device 200 could detect the presence of waste (feces) in the intestines, and a therapy (such as a sphincter opening therapy) could be used to facilitate the excretory process to relieve problems associated with rectal incontinence. Use of device 200 at or near a patient's bladder could be useful to obtain data to treat a urinary disorder of the patient, including potential problems with urination. For example, and regarding potential instances of urinary incontinence, device 200 could detect the presence of urine within the bladder, and a therapy (such as a sphincter opening therapy) could be used to facilitate the excretory process to relieve problems associated with urinary incontinence. In addition, and if device 200 is used in connection with a patient's heart, the data could be useful to treat a cardiac disorder of the patient. This list of organs and discussion regarding the same is not intended to be exhaustive, as various devices 100 of the present disclosure could be used in connection with other luminal organs.

While various embodiments of devices for detecting organ contents and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure.

In addition, disclosure directed to a method and/or process should not be limited to the performance of their steps in the order written. Such sequences may be varied and still remain within the scope of the present disclosure.

The invention claimed is:

1. A device for detecting organ contents, the device comprising:
a body having a detector coupled directly to the body, and at least one detector aperture defined within the body and the at least one detector aperture positioned outside and immediately adjacent the detector, the detector comprising a pair of detection electrodes and a pair of excitation electrodes and the at least one detector aperture sized and shaped to minimize interference that would compromise data obtained by the detector, the at least one detector aperture extending a length from a start of one electrode of the pair of detection electrodes or the pair of excitation electrodes to a start of another electrode of the pair of detection electrodes or the pair of excitation electrodes;
the body configured for external placement at or near an outside of an organ, but not within or surrounding the organ or within a lumen thereof, and the detector configured to both detect a presence or absence of contents within the lumen of the organ using impedance and to distinguish between any contents detected over time based on conductance data by obtaining first conductance data when solid contents are within the lumen, by obtaining second conductance data when liquid contents are within the lumen, and identifying a difference between the first conductance data and the second conductance data.

2. The device of claim 1, wherein the body is configured as a patch and the organ is selected from a group consisting of a stomach, an intestine, a bladder, and a lung.

3. The device of claim 1, wherein the detection electrodes of the detector are positioned on the body in between the pair of excitation electrodes of the detector.

4. The device of claim 3, wherein the pair of excitation electrodes are spaced apart from one another sufficient to generate a field that extends to an inside of the organ.

5. The device of claim 4, wherein the pair of detection electrodes is capable of detecting the field generated by the pair of excitation electrodes.

6. The device of claim 1, wherein the detector is operable to detect whether or not an inside of the organ has a liquid content therein.

7. The device of claim 6, wherein the detector is operable to detect changes in an amount of the liquid content inside of the organ.

8. The device of claim 1, wherein the detector is operable to detect whether or not an inside of the organ has a solid content therein.

9. The device of claim 8, wherein the detector is operable to detect changes in an amount of the solid content inside of the organ.

10. The device of claim 1, further comprising:
an adhesive pad coupled to the body, the adhesive pad configured to secure the device to the outside of the organ.

11. The device of claim 1, further comprising:
at least one suture aperture defined within the body, the at least one suture aperture sized and shaped to receive at least one suture therethrough to secure the device to the outside of the organ.

12. The device of claim 1, further comprising:
a power source coupled directly to the body and operably connected to the detector, the power source configured to provide power to the detector so to operate the detector.

13. The device of claim 1, further comprising:
an internal memory coupled directly to the body and operably connected to the detector, the internal memory operable to store conductance data obtained by the detector.

14. The device of claim 11, wherein the body further comprises one or more tabs, wherein the at least one suture aperture is defined within the one or more tabs.

15. A method for using a device, the method comprising the steps of:
positioning the device at or near an outside of an organ of a patient within the patient's body, but not within the organ or within a lumen of said organ, the device comprising a body having a detector coupled directly to the body, a power source coupled directly to the body and operably connected to the detector, and at least one detector aperture defined within the body and positioned outside the detector, the detector comprising a pair of detection electrodes and a pair of excitation electrodes, the at least one detector aperture extending a length from a start of one electrode of the pair of detection electrodes or the pair of excitation electrodes to a start of another electrode of the pair of detection electrodes or the pair of excitation electrodes, the power source configured to provide power to the detector so to operate the detector, the at least one detector aperture sized and shaped to minimize interference that would compromise data obtained by the detector, and the detector configured to both detect a presence or absence of contents within the lumen of the organ using impedance and distinguish between any contents detected over time based on conductance data by obtaining first conductance data when solid contents are within the lumen, by obtaining second conductance data when liquid contents are within the lumen, and identifying a difference between the first conductance data and the second conductance data; and operating the device to detect contents within the lumen of the organ and distinguish between any contents detected therein over time.

16. The method of claim 15, wherein the operating step is performed by activating the detector to obtain conductance data, the conductance data indicative of the contents on the lumen of the organ.

17. The method of claim 15, wherein the positioning step is performed to position the device at or near the outside of an organ selected from a group consisting of a stomach, an intestine, a bladder, a lung, and a heart.

18. The method of claim 17, wherein the operating step yields conductance data from the detector, the conductance data indicative of a change in an amount of a liquid content on the inside of the organ.

19. The method of claim 15, further comprising: administering a therapy to the patient based upon the contents detected on an inside of the organ.

20. A device for detecting organ contents, the device comprising:
a body having a detector, a power source coupled directly to the body and operably connected to the detector, an internal memory coupled directly to the body and operably connected to the detector, and a transmitter coupled directly to the body, wherein the body is configured as a patch, the power source is configured to provide power to the detector so to operate the detector, the internal memory is operable to store conductance data obtained by the detector, the transmitter operable to transmit conductance data to an external system, and the detector comprises a pair of detection electrodes positioned on the body in between a pair of excitation electrodes;

a pair of detector apertures on either side of the detector, one detector aperture of the pair of detector apertures disposed on a side of the detector, and the other detector aperture from the pair of detector apertures disposed on another side of the detector, each detector aperture of the pair of detector apertures defined within the body;

each of the detector apertures extending a length from a start of one electrode of the pair of detection electrodes or the pair of excitation electrodes to a start of another electrode of the pair of detection electrodes or the pair of excitation electrodes;

the body configured for external placement at or near an outside of an organ, but not within or surrounding the organ or within a lumen thereof, and the detector configured to both detect a presence or absence of contents within the lumen of the organ using impedance and distinguish between any contents detected therein over time based on conductance data by obtaining first conductance data when solid contents are within the lumen, by obtaining second conductance data when liquid contents are within the lumen, and identifying a difference between the first conductance data and the second conductance data;

wherein the pair of excitation electrodes are spaced apart from one another on the body sufficient to generate a field that extends into the lumen of the organ.

* * * * *